(12) United States Patent
Modi

(10) Patent No.: US 6,214,375 B1
(45) Date of Patent: Apr. 10, 2001

(54) PHOSPHOLIPID FORMULATIONS

(75) Inventor: Pankaj Modi, Ancaster (CA)

(73) Assignee: Generex Pharmaceuticals, Inc., Toronto (CA)

( * ) Notice: Subject to any disclaimer, the term of this patent is extended or adjusted under 35 U.S.C. 154(b) by 0 days.

(21) Appl. No.: 09/277,600

(22) Filed: Mar. 29, 1999

Related U.S. Application Data

(63) Continuation-in-part of application No. 08/680,826, filed on Jul. 16, 1996, now abandoned.

(51) Int. Cl.⁷ .......................... A61K 9/127; A61K 51/00; A61K 38/16

(52) U.S. Cl. ................ 424/450; 424/1.11; 514/8

(58) Field of Search ................. 514/8; 424/1.1, 424/450

(56) References Cited

U.S. PATENT DOCUMENTS

| | | | |
|---|---|---|---|
| 4,614,730 | 9/1986 | Hansen et al. | 514/3 |
| 4,708,861 | 11/1987 | Popescu et al. | 424/1.1 |
| 4,772,471 | 9/1988 | Vanlerberghe et al. | 424/450 |
| 4,830,857 | 5/1989 | Handjani et al. | 424/450 |
| 4,839,111 | 6/1989 | Huang | 264/4.6 |
| 4,921,757 | 5/1990 | Wheatley et al. | 428/402.2 |
| 5,006,343 | 4/1991 | Benson et al. | 424/450 |
| 5,147,723 | 9/1992 | Wallach | 428/402.2 |
| 5,234,767 | 8/1993 | Wallach | 428/402.2 |
| 5,260,065 | 11/1993 | Mathur et al. | 424/450 |
| 5,643,600 | 7/1997 | Mathur | 424/450 |

*Primary Examiner*—Hankyel T. Park
(74) *Attorney, Agent, or Firm*—Debra Z. Anderson; Eckert Seamans Cherin & Mellott, LLC

(57) ABSTRACT

A liposome pharmaceutical composition is provided. The liposomes are comprised of a medicinally active agent, at least three phospholipids and at least two biodegradable polymers. The liposomes can be used for delivery of various cosmetics and drugs, and can be administered orally, topically or by injection.

7 Claims, No Drawings

PHOSPHOLIPID FORMULATIONS

CROSS REFERENCE TO RELATED APPLICATIONS

This application is a continuation-in-part of application Ser. No. 08/680,826, filed Jul. 16, 1996 and now abandoned.

FIELD OF THE INVENTION

The present invention relates to improved delivery of medicinally active compounds into the body. In particular it relates to production of stable liposomes for delivery of cosmetics, drugs, enzymes, growth factors, hormones, interferons, interleukins, moisturizers, peptides, proteins, and steroids. A variety of administration techniques, e.g. oral, injection, topical, may be used, depending on the medicinally active ingredient.

BACKGROUND OF THE INVENTION

Drugs, to be effective must be present at the site of action in an effective concentration for a desired period of time. Oral and parenteral administration of drugs relies on the blood circulation to carry the drugs to the target organs. Consequently, the drug is distributed throughout the body and deposited in all organs, which often lead to unwanted side effects. Attempts have been made to favourably influence drug distribution by combining the drug with a "carrier". Among the variety of carriers, liposomes, due to their composition and compatibility with the living organism, seem to have a good potential for selective drug delivery.

It is believed that a substance will have a different destiny when delivered using a liposome rather than by commercially used carriers (sometimes known as excipients), which, due to their composition are foreign to the living organism. Liposomes are made of similar components of cell membranes, and are compatible with the skin superficial layer structure. According to one source, the horny skin layer can be compared to a wall, where keratinized cells represent the bricks, and intracellular lipids the cement which keeps them together. Lipids, lying in lamellae, show a bilayer structure similar to that of biological membranes. They have a lipidic layer enclosed in a water layer. The function of the lipid layer is double: on the one hand it represents the most important part of the barrier of the cutaneous permeability, on the other hand it maintains the hydration of the skin, indispensable for the integrity of the skin. It is believed that liposomes, made of phospholipidic fractions which absorb water, act both as a water carrier and as a reintegrator of permeability, since they interact with the lamellar lipids of the horny skin layer. Moreover, the liposome vesicle has the function of "carrier", that is, it releases the encapsulated active substances both through diffusion from its walls and through spill when it opens.

Materials like vaccines, hormones, enzymes, interferons, interleukins, are rapidly inactivated when injected into body and when they enter systemic circulation. Accumulation of these active substances in the body, to generate a superior response or therapeutic effect, is not satisfactory and systemic side effects can occur frequently. Incorporating such materials into liposomes can increase their efficacy several folds and provides superior therapeutic effect.

Interest in the use of liposomes in dermato-cosmetology has increased in the recent years, mainly for two reasons: the particular affinity of liposomes with the skin, and the fact that they are applied directly on the part where they are destined. The advantages of this kind of transportation into the skin include release of the active ingredients at different levels in the skin, longer contact with the cutaneous layers, and reduced systemic absorption. Release of the active ingredient mainly occurs in the multilamellar liposomes, which allows a slower release of the active ingredient in the chosen site, with a so-called depot effect, which is very useful in order to streamline the effects on the skin.

The clinical use of liposomes has been delayed because of difficulties in mass production, sterilization, stability and safety. The present invention is aimed at production of stable liposomes for delivery of medicinally active ingredients.

Molecular weights indicated herein are weight average molecular weights (Mw) and can be determined by known light scattering methods or gel filtration chromatography methods. Light scattering methods are preferred.

DISCLOSURE OF THE INVENTION

Accordingly the present invention provides a formulation comprising i) at least one medicinally active ingredient, ii) at least three compounds selected from the group consisting of egg phosphatidylcholine (PC) dilauryl phosphatidylcholine (DLPC), dimyristoyl phosphatidylcholine (DMPC), dipalmitoyl phosphatidylcholine(DPPC), dioleoyl phosphatidylcholine (DOPC), dimyristoyl phosphatidylglycerol (DMPG), dipalmitoyl phosphatidylglycerol(DPPG), dimyristoyl phosphatidic acid (DMPA), dipalmitoyl phosphatidic acid (DPPA), dipalmitoyl phosphatidylethanolamine (DPPE), distearoyl phosphatidylcholine (DSPC), brain phosphatidylserine (PS), brain sphingomyelin (SM), cholesterol (C), cardiolipin (CL), trioctanoin (TC), triolein (TO), soy phosphatidylcholine, poly(adenylic acid), phosphatidylethanolamine (PE), phosphatidyl glycerol (PG), phosphatidyl inositol (PI), sphingosine, cerebroside (glycolipid), and iii) at least one biodegradable polymer selected from the group consisting of copolymers of sucrose and epichlorohydrin having molecular weights of from 70 000 to 400 000, branched hydrophilic polymers of sucrose having molecular weights of from 70 000 to 400 000, polyethylene glycols having molecular weights of from 1000 to 100 000, polyvinyl alcohols having molecular weights of from 70 000 to 110 000, methoxypolyethylene glycol, ethoxypolyethylene glycol, polyethylene oxide, polyoxyethylene, polyoxypropylene, cellulose acetate, sodium alginate, N,N-diethylaminoacetate, block copolymers of polyoxyethylene and polyoxypropylene, polyvinyl pyrrolidone, polyoxyethylene X-lauryl ether wherein X is from 9 to 20, and polyoxyethylene sorbitan esters.

The letter combinations in parentheses are abbreviations used elsewhere in this specification.

It is to be understood that the term "egg phosphatidylcholine" comprises combinations of substantially saturated phosphatidylcholines, e.g. combinations of 99% saturated Phospholipon H (trade mark) and 90% saturated Phospholipon G (trade mark) in ratios of 70:30 to 95:5 Phospholipon H:Phospholipon G.

In another embodiment the formulation has at least two biodegradable polymers.

In yet another embodiment the combinations of compounds are selected from the group consisting of: i) brain phosphatidylserine, cholesterol, triolein and phosphatidylethanolamine, ii) egg phosphatidylcholine, distearoyl phosphatidylcholine, cholesterol and triolein, iii) cholesterol, cardiolipin, poly(adenylic acid) and triolein, iv) egg phosphatidylcholine, distearoyl phosphatidylcholine, cholesterol and trioctanoin, v) egg phosphatidylcholine, cholesterol, trioctanoin and phosphatidyl glycerol, vi) egg phosphatidylcholine, cholesterol, cardiolipin and triolein, vii) dioleoyl phosphatidylcholine, cholesterol, cardiolipin and triolein, viii) egg phosphatidylcholine, cholesterol, brain phosphatidylserine and triolein, ix) dioleoyl phosphatidylcholine, brain phosphatidylserine, cholesterol and triolein, x) egg phosphatidylcholine, dipalmitoyl phosphatidylglycerol, cholesterol and trioctanoin, xi) dimyristoyl phosphatidylcholine, dipalmitoyl phosphatidylcholine, distearoyl phosphatidylcholine and triolein, xii) egg phosphatidylcholine, dipalmitoyl phosphatidylcholine, distearoyl phosphatidylcholine and trioctanoin, xiii) phosphatidylcholine, cholesterol, brain phosphatidylserine and triolein, xiv) phosphatidylethanolamine, cholesterol cardiolipin and triolein, xv) phosphatidylcholine, cholesterol, trioctanoin and dipalmitoyl phosphatidylethanolamine, xvi) dimyristoyl phosphatidylcholine, dipalmitoyl phosphatidylcholine, distearoyl phosphatidylcholine and triolein, xvii) phosphatidylcholine, phosphatidylethanolamine, cholesterol, brain phosphatidylserine and triolein, xviii) phosphatidylcholine, phosphatidylthanolamine, cholesterol, cardiolipin and triolein, xix) phosphatidylcholine, dioleoyl phosphatidylcholine, cholesterol, cardiolipin and triolein, xx) phosphatidylcholine, dioleoyl phosphatidylcholine, cholesterol, brain phosphatidylserine and triolein, xxi) phosphatidylcholine, dimyristoyl phosphatidylcholine, dipalmitoyl phosphatidylcholine, distearoyl phosphatidylcholine and triolein and xxii) phosphatidylcholine, cholesterol, phosphatidylcholine ethanloamine and triolein.

Preferred weight ratios of these combinations are shown in parentheses: PE/C/PS/TO (4.5/4.5/1/1); PC/C/DSPC/TC (4.1/1.9/1/1); PE/C/CL/TO (4.5/4.5/1/1); PC/C/TC/DPPE (4.1/1.9/6.6/1); PC/C/PS/TO (4.5/4.5/2/1); PC/C/CL/TO (4.5/4.5/1/1); DOPC/C/CL/TO (4.5/4.5/1/1); PC/C/PG/TC (5/4/1/1); DOPC/C/PS/TO (5/5/1/1); PC/C/DPPG/TC (5/4/1/1); DMPC/DPPC/DSPC/TO (5/6/10/2); PC/DSPC/C/DPPC/TC (5/5/1/5/1); PC/PE/C/PS/TO (4.5/4.5/4.5/1/1); PC/PE/C/CL/TO (4.5/4.5/4.5/4.5/1/1); PC/DOPC/C/CL/TO (4.5/4.5/4.5/1/1); PC/DOPC/C/PS/TO (5/5/5/1/1); PC/DMPC/DPPC/DSPC/TO (5/5/6/10/2); and PC/C/PE/TO (4/2/1/1).

The above ratios refer to specific preferred ratios. It is to be understood that variations in the ratios may be made to effect the desired long release characteristics. For example, each of the compounds in the combinations are preferably present in concentrations of between about 5 and about 55% of the combination. For example phosphatidylcholine, phosphatidylcholine ethanolamine, dioleoyl phosphatidylcholine, trioctanoin and cholesterol typically may be present in concentrations of 5 to 55% of the phospholipid combination; dimyristoyl phosphatidylcholine, dipalmitoyl phosphatidylcholine and distearoyl phosphatidylcholine typically may be present in concentrations of 15 to 50% of the phospholipid combination; and brain phosphatidylserine, triolein, cardiolipin, dipalmitoyl phosphatidylethanolamine, dipalmitoyl phosphatidylglycerol, and phosphatidyl glycerol typically may be present in concentrations of 5 to 15% of the phospholipid combination.

Those skilled in the art will be aware of the general effect of individual compounds and this is useful in determining the selection of compounds in any particular composition. For example long chain fatty acids such as phosphatidyl glycerol or triolein are useful for enhancing the penetration of the composition into the skin and for solubilization of drugs. Substantially saturated phosphatidylcholine is useful in stabilizing liposomes as they are less prone to oxidation. The presence of phosphatidylcholine also makes manufacture easier because it is not necessary to make the formulation in a nitrogen atmosphere. Additionally, for example, cardiolipin, brain phosphatidylserine and brain sphingomyelin are charged lipids and tend to concentrate the formulation on the desired site of attack.

The preferred liposome formulation is prepared using stabilizers, absorption enhancers, and antioxidants in addition to the phospholipids, biodegradable polymer, and medicinally active ingredients.

The formulations of the present invention may be in lamellar, vesicle or other form, depending on the particular composition of the formulation. The lamellae, vesicles or other forms may be coated with at least one biodegradable polymer, preferably two polymers selected from the group consisting of copolymers of sucrose and epichlorohydrin having molecular weights of from 70 000 to 400 000, branched hydrophilic polymers of sucrose having molecular weights of from 70 000 to 400 000, polyethylene glycols having molecular weights of from 1000 to 100 000, polyvinyl alcohols having molecular weights of from 70 000 to 110 000, methoxypolyethylene glycol, ethoxypolyethylene glycol, polyethylene oxide, polyoxyethylene, polyoxypropylene, cellulose acetate, sodium alginate, N,N-diethylaminoacetate, block copolymers of polyoxyethylene and polyoxypropylene, polyvinyl pyrrolidone, polyoxyethylene X-lauryl ether wherein X is from 9 to 20, and polyoxyethylene sorbitan esters.

It will be recognized by those skilled in the art that for many pharmaceutical compositions it is usual to add at least one antioxidant to prevent degradation and oxidation of the medicinally active ingredients. Preferred antioxidants may be selected from the group consisting of ascorbic acid, tocopherol and deteroxime mesylate.

In another embodiment, an antifungal, antimicrobial agent selected from the group consisting of ethyl paraben, methyl paraben, propyl paraben and combinations thereof may also be added to the composition.

In another embodiment the formulation contains at least one absorption enhancer, especially absorption enhancers selected from the group consisting of Na-salicylate-chenodeoxy cholate, Na deoxycholate, polyoxyethylene 9-lauryl ether, chenodeoxy cholate-deoxycholate and polyoxyethylene 9-lauryl ether, monoolein, Na tauro-24,25-dihydrofusidate, Na taurodeoxycholate, Na glycochenodeoxycholate, oleic acid, linoleic acid, linolenic acid.

Polymeric absorption enhancers may also be added to the formulation, e.g. polyoxyethylene ethers, polyoxyethylene sorbitan esters, polyoxyethylene 10-lauryl ether, polyoxyethylene 16-lauryl ether, azone (1-dodecylazacycloheptane-2-one), and sodium chloride, sodium bicarbonate in combination with the above mentioned materials.

Examples of the medicinally active ingredients include insulin, heparin, hirugen, hirulos, hirudin; vaccines such as influenza virus vaccine, pneumonia vaccine, hepatitis A vaccine, hepatitis B vaccine, and hepatitis C vaccine, cholera toxin B-subunit, influenza vaccine virus, typhoid vaccine, plasmodium falciparum vaccine, diphtheria vaccine, tetanus, herpes simpex virus vaccine, tuberculosis vaccine, HIV vaccine, bordetela pertussis vaccine, measles vaccine, mumps vaccine and rubella vaccine (MMR), bacterial toxoids, vaccinia virus, adenovirus vaccine, canary vaccine vaccine, polio vaccine virus, bacillus calmette guerin (BCG), klebsiella pneumonia vaccine, HIV envelope glycoproteins,; hormones such as bovine somatropine, oestrogen, androgens, prostaglandins, somatotropins, enzymes such as thyroids, pituitary, digestive, α-, β- and γinterferons, tuftsin, interleukins, insulin and insulin like growth factors, cytokines, steroids, terpenoids, triterpenes, retinoids; anti-ulcer $H_2$ receptor antagonists, anti-ulcer drugs, hypoglycaemic agents, moisturizers, cosmetics and drugs.

Examples of bacterial toxoids are tetanus, diphtheria, pseudomonas A, mycobacterium tuberculosis. Examples of HIV envelope glycoproteins are gp 120 and gp 160 for AIDS vaccines. Examples of anti-ulcer $H_2$ receptor antagonists are ranitidine, cimetidine and famotidine, and other anti-ulcer drugs are omparazide, cesupride and misoprostol. An example of a hypoglycaemic agent is glizipide. Insulin is used for the control of diabetes.

As will be understood by those skilled in the art, two or more pharmaceutical agents may be combined for specific effects. The necessary amounts of active ingredient can be determined by simple experimentation. Specific pharmaceutical agents which may be used in this invention are insulin, heparin, low molecular weight heparin, hirugen, hirulos and hirudin.

The method of making the formulation is straightforward. Typically the combination of compounds are dissolved in an organic solvent such as ethanol or chloroform/methanol. The drug is dissolved in water or a buffer solution and vigorously mixed. The liposome forms instantaneously on vigorous stirring, sonication or agitation. The medicinally inactive ingredients, e.g. any antioxidants, inorganic salts, protective polymers, protease inhibitors, absorption enhancers and other ingredients, e.g. colouring matter, flavourings, are then added and mixed until the solution is homogeneous. Typically the ratio of compounds to medicinally active ingredient may vary from 50:1 to 1:1.

In the selection of a suitable absorption enhancing compound combination, it has been found that the amount of total absorption enhancing compound should be less than about 10 wt./wt. % of the formulation and preferably from 1 to 5 wt./wt. %. Frequent use or prolonged use of higher concentrations of absorption enhancing compounds are likely to be harmful to linings and tissues in the gastrointestinal tract, and may cause diarrhoea. It is believed that the optimum range for most combinations is from 1.5 to 3.5 wt./wt. %.

The invention may also be better understood by reference to the following examples:

EXAMPLE I

Compositions containing Ponceau-S dye were prepared using following procedure:

Compositions shown in Table I were dissolved in 15 ml of chloroform/methanol (2:1 vol/vol). The resulting clear solution was introduced into a 250 ml round bottom flask with a ground-glass neck. The flask was attached to a rotary evaporator, rotated at about 100 rpm to remove solvent at a reduced pressure. The rotation of flask was continued until all the liquid evaporated and dry uniform film was obtained on the walls of the flask. The flask was removed from the rotary evaporator equipment and was attached to a vacuum line for the complete removal of the solvent. After releasing the vacuum, the flask was flushed with nitrogen, and 0.1% Ponceau-S dye solution prepared in 5 ml of distilled water containing 0.3% polyethylene glycol having a molecular weight of 10 000, 0.3% ethylhydroxy cellulose (1:1), 0.1% monoolein, 0.1% linoleic acid, and 0.2% tocopherol. The solution was poured in the flask and 0.5 g glass beads were added. The flask was rotated slowly for 30 minutes until all the phospholipid was removed from the walls of the flask. A homogenous milky white suspension was formed. The suspension was allowed to stand at room temperature for 2 hrs in order to allow swelling to take place. The resulting suspension was spun at 12 000 G for 10 minutes in a bench centrifuge. A pellet was formed, which was then removed and stored at room temperature for analysis.

The composition containing Ponceau-S dye was analyzed for % encapsulation using Protamine aggregation method:

0.1 ml of liposomal suspension (20 mg/ml lipid) in 10 ml 0.9% NaCl solution in a glass centrifuged tube. To this suspension was added 0.2 ml protamine solution and allowed to stand for 5 min and was spun at 2000 G for 20 minutes at room temperature. Supernatant was analyzed for free, untrapped materials using UV spectroscopy (dye concentration was measured at 510 and 560 nm). The resulting pellet was collected and 0.6 ml 10% Triton-X 100 added to dissolve liposomal material. The solubilized material was further diluted with 5 ml saline solution and the resulting liquid was assayed for entrapped material (dye) by UV spectroscopy at 510 and 560 nm. Table I outlines % Ponceau-S dye in various liposomes.

The percent dye entrapped is calculated as (the dye concentration in the liposome composition minus the dye concentration in supernatant) divided by the dye concentration in the liposome composition x100.

TABLE I

| Liposome Composition | % dye entrapped |
| --- | --- |
| PC/PE/C/PS/TO (4.5/4.5/4.5/1/1) | 87% |
| PE/C/PS/TO (4.5/4.5/1/1) | 87% |
| PC/C/DSPC/TC (4.1/1.9/1/1) | 89% |
| PC/PE/C/CL/TO (4.5/4.5/4.5/1/1) | 87% |
| PE/C/CL/TO (4.5/4.5/1/1) | 87% |
| PC/C/TC/DPPE (4.1/1.9/6.6/1) | 84% |
| PC/C/PS/TO (4.5/4.5/2/1) | 84% |
| PC/C/CL/TO (4.5/4.5/1/1) | 85% |
| PC/DOPC/C/CL/TO (4.5/4.5/4.5/1/1) | 82% |
| DOPC/C/CL/TO (4.5/4.5/1/1) | 82% |
| PC/C/PG/TC (5/4/1/1) | 78% |
| PC/DOPC/C/PS/TO (5/5/5/1/1) | 80% |
| DOPC/C/PS/TO (5/5/1/1) | 80% |
| PC/C/DPPG/TC (5/4/1/1) | 75% |
| PC/DMPC/DPPC/DSPC/TO (5/5/6/10/2) | 89% |
| DMPC/DPPC/DSPC/TO (5/6/10/2) | 89% |
| PC/DSPC/C/DPPC/TC (5/5/1/5/1) | 77% |

The release characteristics of one of the phospholipid composition was investigated by solubilizing the phospholipid composition in a dilute (1–2%) Triton-X 100 solution. The composition containing dye (100 μL) was diluted with 3 ml saline and placed in glass tube. To this solution 100 μL of 1–2% Triton-X 100 solution was added. The resulting solution was mixed to obtain a homogenous solution, and centrifuged. The supernatant was placed in a glass UV cuvette and absorbance readings were taken at 510 and 560 nm at regular time intervals. The results are shown in Table II.

TABLE II

| Time (Minutes) | % Dye Released |
| --- | --- |
| 10 | 7.5% |
| 30 | 14.3% |
| 60 | 18.9% |
| 120 | 25% |

TABLE II-continued

| Time (Minutes) | % Dye Released |
|---|---|
| 180 | 33.3% |
| 240 | 40% |
| 300 | 47.5% |

EXAMPLE II

In order to demonstrate the efficacy of the formulation of the present invention in the field of dermato-cosmetology, a composition containing PE/C/PS/TO in ratio of (5/5/2/1) was dissolved in 15 ml of chloroform/methanol (2:1 vol/vol). The resulting clear solution was introduced into a 250 ml round bottom flask with a ground-glass neck. The flask was attached to a rotary evaporator, rotated at about 100 rpm to remove solvent at a reduced pressure. The rotation of flask was continued until all the liquid evaporated and dry uniform film was obtained on the walls of the flask. The flask was removed from the rotary evaporator equipment and was attached to vacuum line for the complete removal of the solvent. After releasing the vacuum, the flask was flushed with nitrogen and 500 mg lidocaine solution prepared in 5 ml of distilled water containing 0.3% polyethylene glycol having a molecular weight of 10 000, 0.3% ethylhydroxy cellulose (1:1), 0.1% monoolein, 0.1% linoleic acid, and 0.2% tocopherol. The solution was poured in the flask and 0.5 g glass beads were added. The flask was rotated slowly for 30 min until all the PE/C/PS/TO was removed from the walls of the flask to give a homogenous milky white suspension. The suspension was allowed to stand at room temperature for 2 hrs in order to allow swelling to take place. The resulting suspension was spun at 12 000 G for 10 minutes in a bench centrifuge. A pellet was formed, which was then removed and stored at room temperature for analysis.

The lidocaine concentration was calculated by estimating amount of lidocaine in the PE/C/PS/TO solution and untrapped lidocaine in supernatant. The liposomal lidocaine suspension was then stored in a bottle at room temperature. Ten healthy male guinea pigs weighing 500–700 g were anaesthetized by intraperitonial injection of 0.2 ml of sodium pentobarbital. Lidocaine cream (5 guinea pigs) and the present PE/C/PS/TO lidocaine (5 guinea pigs) were applied to tail, leg and back areas. After about 4.5 hours tissue samples (epidermis, dermis, and subcutaneous layers) were collected and processed for lidocaine concentration estimation. Tissue samples from each layer were weighed and approximately equal amounts were placed in a phosphate buffer (pH 7.4), homogenized, and centrifuged at 20 000 G for minutes. Supernatant was collected and was analyzed for lidocaine concentration using standard HPLC technique. The results for tissue concentration of lidocaine are shown in Table III, overleaf, which compares 2% Lidocaine Cream (control sample, not of the present invention) and 2% liposomal Lidocaine Cream (an embodiment of the present invention) of the above composition.

TABLE III

| Tissue Sample (after 4.5 Hrs) | Regular Lidocaine ($\mu$g/g tissue) | Liposomal Lidocaine ($\mu$g/g tissue) |
|---|---|---|
| Epidermis | 75.87 | 198.8 |
| Dermis | 22.61 | 48.1 |
| Subcutaneous | 5.32 | 3.9 |
| Plasma | 0.077 | 0.023 |

EXAMPLE III

In order to further demonstrate a method of making a formulation of the present invention, which is suitable for scale-up to industrial quantities, 8 g of a composition containing PC/C/Phospholipon G/PE/TO in ratio of (2/2/2/1/1) was dissolved in 6 g of 100% ethanol at a temperature of 60° C. to 65° C., in a beaker. 0.2 g of tretinoin-A (trade mark: Ratinyl-A) was added to the beaker and dissolved at high speed using a magnetic stirrer rotating at about 1000 rpm. 86.8 g distilled water was added at 60° C. slowly to the alcohol solubilized mixture, while stirring at 1000 rpm at a temperature of 60° C. to 65° C. The resulting reaction mixture was cooled to room temperature after completion of the addition of water, while continuing to stir at 1000 rpm. A multi-lamellar liposome suspension formed spontaneously. The size of the liposome suspension was measured by flow cytometer, using laser light scattering techniques, and the sizes measured were from 50 nm to 1 $\mu$m. The percent encapsulation of tretinoin was determined using HPLC equipped with a UV detector and found to be 91.5%.

What is claimed is:

1. A liposomal formulation comprising i) at least one medicinally active ingredient, ii) at least three compounds selected from the group consisting of egg phosphatidylcholine, dilauryl phosphatidylcholine, dimyristoyl phosphatidylcholine, dipalmitoyl phosphatidylcholine, dioleoyl phosphatidylcholine, dimyristoyl phosphatidylglycerol, dipalmitoyl phosphatidic acid, dipalmitoyl phosphatidic acid, dipalmitoyl phosphatidylethanolamine, distearoyl phosphatidylcholine, brain phosphatidylserine, brain sphingomyelin, cholesterol, cardiolipin, trioctanoin, triolein, soy phosphatidylcholine, poly(adenylic acid), phosphatidylethanolamine, phosphatidyl glycerol, phosphatidyl inositol, sphingosine, cerebroside (glycolipid), and iii) at least two biodegradable polymers selected from the group consisting of copolymers of sucrose and epichlorohydrin having molecular weights of from 70 000 to 400 000, branched hydrophilic polymers of sucrose having molecular weights of from 70 000 to 400 000, polyethylene glycols having molecular weights of from 1000 to 100 000, polyvinyl alcohols having molecular weights of from 70 000 to 110 000, methoxypolyethylene glycol, ethoxypolyethylene glycol, polyethylene oxide, polyoxyethylene, polyoxypropylene, cellulose acetate, sodium alginate, N,N-diethylaminoacetate, block copolymers of polyoxyethylene and polyoxypropylene, polyvinyl pyrrolidone, polyoxyethylene X-lauryl ether wherein X is from 9 to 20, and polyoxyethylene sorbitan esters.

2. A formulation according to claim 1 wherein there are at least three biodegradable polymers in the formulation.

3. A formulation according to claim 1 wherein the compound combinations are selected from the group consisting of:

i) brain phosphatidylserine, cholesterol, triolein and phosphatidylethanolamine, ii) egg phosphatidylcholine, distearoyl phosphatidylcholine, cholesterol and triolein, iii) cholesterol, cardiolipin, poly(adenylic acid) and triolein, iv) egg phosphatidylcholine, distearoyl phosphatidylcholine, cholesterol and trioctanoin, v) egg phosphatidylcholine, cholesterol, trioctanoin and phosphatidyl glycerol, vi) egg phosphatidylcholine, cholesterol, cardiolipin and triolein, vii) dioleoyl phosphatidylcholine, cholesterol, cardiolipin and triolein, viii) egg phosphatidylcholine, cholesterol, brain phosphatidylserine and triolein, ix) dioleoyl phosphatidylcholine, brain phosphatidylserine, cholesterol and triolein, x) egg phosphatidylcholine, dipalmitoyl phosphatidylglycerol, cholesterol and trioctanoin, xi) dimyristoyl phosphatidylcholine, dipalmitoyl phosphatidylcholine, distearoyl phosphatidylcholine and triolein, xii) egg phosphatidylcholine, dipalmitoyl phosphatidylcholine, distearoyl phosphatidylcholine and trioctanoin, xiii) phosphatidylcholine, cholesterol, brain phosphatidylserine and triolein, xiv) phosphatidylethanolamine, cholesterol cardiolipin and triolein, xv) phosphatidylcholine, cholesterol, trioctanoin and dipalmitoyl phosphatidylethanolamine, xvi) dimyristoyl phosphatidylcholine, dipalmitoyl phosphatidylcholine, distearoyl phosphatidylcholine and triolein, xvii) phosphatidylcholine, phosphatidylethanolamine, cholesterol, brain phosphatidylserine and triolein, xviii) phosphatidylcholine, phosphatidylthanolamine, cholesterol, cardiolipin and triolein, xix) phosphatidylcholine, dioleoyl phosphatidylcholine, cholesterol, cardiolipin and triolein, xx) phosphatidylcholine, dioleoyl phosphatidylcholine, cholesterol, brain phosphatidylserine and triolein, xxi) phosphatidylcholine, dimyristoyl phosphatidylcholine, dipalmitoyl phosphatidylcholine, distearoyl phosphatidylcholine and triolein and xxii) phosphatidylcholine, cholesterol, phosphatidylcholine ethanloamine and triolein.

4. A formulation according to claim 2 wherein the compound combinations are selected from the group consisting of:

i) brain phosphatidylserine, cholesterol, triolein and phosphatidylethanolamine, ii) egg phosphatidylcholine, distearoyl phosphatidylcholine, cholesterol and triolein, iii) cholesterol, cardiolipin, poly(adenylic acid) and triolein, iv) egg phosphatidylcholine, distearoyl phosphatidylcholine, cholesterol and trioctanoin, v) egg phosphatidylcholine, cholesterol, trioctanoin and phosphatidyl glycerol, vi) egg phosphatidylcholine, cholesterol, cardiolipin and triolein, vii) dioleoyl phosphatidylcholine, cholesterol, cardiolipin and triolein, viii) egg phosphatidylcholine, cholesterol, brain phosphatidylserine and triolein, ix) dioleoyl phosphatidylcholine, brain phosphatidylserine, cholesterol and triolein, x) egg phosphatidylcholine, dipalmitoyl phosphatidylglycerol, cholesterol and trioctanoin, xi) dimyristoyl phosphatidylcholine, dipalmitoyl phosphatidylcholine, distearoyl phosphatidylcholine and triolein, xii) egg phosphatidylcholine, dipalmitoyl phosphatidylcholine, distearoyl phosphatidylcholine and trioctanoin, xiii) phosphatidylcholine, cholesterol, brain phosphatidylserine and triolein, xiv) phosphatidylethanolamine, cholesterol cardiolipin and triolein, xv) phosphatidylcholine, cholesterol, trioctanoin and dipalmitoyl phosphatidylethanolamine, xvi) dimyristoyl phosphatidylcholine, dipalmitoyl phosphatidylcholine, distearoyl phosphatidylcholine and triolein, xvii) phosphatidylcholine, phosphatidylethanolamine, cholesterol, brain phosphatidylserine and triolein, xviii) phosphatidylcholine, phosphatidylthanolamine, cholesterol, cardiolipin and triolein, xix) phosphatidylcholine, dioleoyl phosphatidylcholine, cholesterol, cardiolipin and triolein, xx) phosphatidylcholine, dioleoyl phosphatidylcholine, cholesterol, brain phosphatidylserine and triolein, xxi) phosphatidylcholine, dimyristoyl phosphatidylcholine, dipalmitoyl phosphatidylcholine, distearoyl phosphatidylcholine and triolein and xxii) phosphatidylcholine, cholesterol, phosphatidylcholine ethanloamine and triolein.

5. A formulation according to claim 1 wherein the medicinally active ingredient is selected from the group consisting of insulin, heparin, hirugen, hirulos, hirudin, influenza virus vaccine, pneumonia vaccine, hepatitis A vaccine, hepatitis B vaccine, and hepatitis C vaccine, cholera toxin B-subunit, influenza vaccine virus, typhoid vaccine, plasmodium falciparum vaccine, diphtheria vaccine, tetanus, herpes simpex virus vaccine, tuberculosis vaccine, Bordetela vaccine, bordetela pertussis vaccine, measles vaccine, mumps vaccine and rubella vaccine (MMR), bacterial toxoids, vaccinia virus, adenovirus vaccine, canary pox vaccine, polio vaccine virus, bacillus calmette guerin (BCG), klebsiella envelope vaccine, HIV envelope glycoproteins, bovine somatropine, oestrogen, androgens, prostaglandins, somatotropins, thyroid enzyme, pituitary enzyme, digestive enzyme, $\alpha$-,$\beta$- and $\gamma$interferons, tuftsin, interleukins, insulin and insulin like growth factors, cytokines, steroids, terpenoids, triterpenes, retinoids, anti-ulcer $H_2$ receptor antagonists, anti-ulcer drugs, hypoglycaemic agents, moisturizers, cosmetics, drugs, tetanus toxoid, diphtheria vaccine toxoid, pseudomonas A toxoid, mycobacterium tuberculosis vaccine toxoid, HIV envelope glycoproteins.

6. A formulation according to claim 2 wherein the medicinally active ingredient is selected from the group consisting of insulin, heparin, hirugen, hirulos, hirudin, influenza virus vaccine, pneumonia vaccine, hepatitis A vaccine, hepatitis B vaccine, and hepatitis C vaccine, cholera toxin B-subunit, influenza vaccine virus, typhoid vaccine, plasmodium falciparum vaccine, diphtheria vaccine, tetanus, herpes simpex virus vaccine, tuberculosis vaccine, Bordetela vaccine, bordetela pertussis vaccine, measles vaccine, mumps vaccine and rubella vaccine (MMR), bacterial toxoids, vaccinia virus, adenovirus vaccine, canary pox vaccine, polio vaccine virus, bacillus calmette guerin (BCG), klebsiella envelope vaccine, HIV envelope glycoproteins, bovine somatropine, oestrogen, androgens, prostaglandins, somatotropins, thyroid enzyme, pituitary enzyme, digestive enzyme, $\alpha$-, $\beta$- and $\gamma$interferons, tuftsin, interleukins, insulin and insulin like growth factors, cytokines, steroids, terpenoids, triterpenes, retinoids, anti-ulcer $H_2$ receptor antagonists, anti-ulcer drugs, hypoglycaemic agents, moisturizers, cosmetics, drugs, tetanus toxoid, diphtheria vaccine toxoid, pseudomonas A toxoid, mycobacterium tuberculosis vaccine toxoid, HIV envelope glycoproteins.

7. A formulation according to claim 3 wherein the medicinally active ingredient is selected from the group consisting of insulin, heparin, hirugen, hirulos, hirudin, influenza virus vaccine, pneumonia vaccine, hepatitis A vaccine, hepatitis B vaccine, and hepatitis C vaccine, cholera toxin B-subunit, influenza vaccine virus, typhoid vaccine, plasmodium falciparum vaccine, diphtheria vaccine, tetanus, herpes simpex virus vaccine, tuberculosis vaccine, Bordetela vaccine, bordetela pertussis vaccine, measles vaccine, mumps vaccine and rubella vaccine (MMR), bacterial toxoids, vaccinia virus, adenovirus vaccine, canary pox vaccine, polio vaccine virus, bacillus calmette guerin (BCG), klebsiella envelope vaccine, HIV envelope glycoproteins, bovine somatropine, oestrogen, androgens, prostaglandins, somatotropins, thyroid enzyme, pituitary enzyme, digestive enzyme, $\alpha$-, $\beta$- and $\gamma$interferons, tuftsin, interleukins, insulin and insulin like growth factors, cytokines, steroids, terpenoids, triterpenes, retinoids, anti-ulcer $H_2$ receptor antagonists, anti-ulcer drugs, hypoglycaemic agents, moisturizers, cosmetics, drugs, tetanus toxoid, diphtheria vaccine toxoid, pseudomonas A toxoid, mycobacterium tuberculosis vaccine toxoid, HIV envelope glycoproteins.

* * * * *